United States Patent [19]

Habib

[11] 4,350,785

[45] Sep. 21, 1982

[54] SILICA-CONTAINING PROTECTIVE ADHESIVE PASTE FOR USE WITH OSTOMY APPLIANCES

[75] Inventor: Wagdi W. Habib, Roselle, Ill.

[73] Assignee: Hollister Incorporated, Libertyville, Ill.

[21] Appl. No.: 266,448

[22] Filed: May 22, 1981

Related U.S. Application Data

[63] Continuation-in-part of Ser. No. 87,664, Oct. 24, 1979, abandoned.

[51] Int. Cl.³ .................... A61F 13/02; A61L 15/06; C08L 5/00
[52] U.S. Cl. ..................................... 524/55; 524/35; 523/111; 523/205; 523/209; 523/334; 128/283
[58] Field of Search ............... 260/17.4 ST, 17.4 CL; 128/283; 523/111, 205, 209, 334; 524/27, 35, 55, 734

[56] References Cited

U.S. PATENT DOCUMENTS

| | | | |
|---|---|---|---|
| 3,640,741 | 2/1972 | Etes | 128/283 |
| 3,980,084 | 9/1976 | Kross . | |
| 4,254,008 | 3/1981 | Krsek | 128/283 |
| 4,258,715 | 3/1981 | Goble | 128/283 |

FOREIGN PATENT DOCUMENTS 1430515 3/1976 United Kingdom ........ 260/17.4 ST

*Primary Examiner*—John Kight, III
*Assistant Examiner*—Nathan M. Nutter

[57] ABSTRACT

Protective adhesive pastes for use with ostomy appliances which are formulated as mixtures of water-absorbing particulate hydrocolloid gums and organic solvent solutions of adhesive film-forming resins are provided with increased resistance to urine and intestinal fluids by incorporating a small amount of colloidal silica, preferably, fumed silica.

14 Claims, No Drawings

SILICA-CONTAINING PROTECTIVE ADHESIVE PASTE FOR USE WITH OSTOMY APPLIANCES

RELATED APPLICATION

This application is a continuation-in-part of copending application Ser. No. 87,664, filed Oct. 24, 1979, now abandoned.

BACKGROUND AND PRIOR ART

Protective adhesive paste preparations for use with ostomy appliances are known and widely used by ostomates. Such preparations are commonly formulated with karaya gum or other hydrocolloid gums. The gums in powder form are mixed with an alcohol or other organic solvent solution of an adhesive film-forming resin. Preparations of this general kind are described in British Pat. No. 1,430,515, and have been sold commercially in the United States and other countries for a number of years.

When the person wearing the ostomy appliance (the ostomate) has difficulty in maintaining a liquid-tight seal between the ostomy appliance and the skin around the stoma an adhesive paste may be of great value. The problem of fluid leakage is aggravated where the skin around the stoma is irregular, or where folds of skin occur in this area. Under such conditions, even though the ostomy device is used with a molded sealing member such as a ring, blanket, or the like, a complete liquid-tight seal cannot be assured. To obtain a more perfect seal the ostomate applies a coating of an adhesive in a ring around the stoma, permits the paste to dry, and then applies the ostomy device. Additional paste may also be applied to the skin-engaging side of the ring or blanket before application.

With ileostomies and colostomies the area around the stoma is exposed to intestinal fluids, which in the case of ileostomies may include gastric juices containing proteolytic enzymes. With urostomies the area around the stoma is exposed to urine. Therefore, in the use of paste preparations, as described above, one problem is that the applied paste is not sufficiently resistant to intestinal fluids or urine. It has been desired to increase the mechanical and adhesive endurance of such adhesive pastes when applied around the stoma, but heretofore no means has been provided for accomplishing this result.

One of the skin irritation problems associated with the use of ostomy appliances is referred to as adhesive trauma, which the stripping of the skin through repeated application and removal of the adhesively-attached ostomy appliance. Adhesive trauma is aggravated by increases in the frequency with which the ostomy device is removed and reapplied. By providing an adhesive paste preparation of greater endurance, it should be possible to reduce the frequency of removal of the ostomy device, thereby reducing skin irritation caused by the skin-stripping effect.

SUMMARY OF INVENTION

The present invention is based in part on the discovery that a new and surprising result is obtained by the incorporation of a small amount of colloidal silica ($SiO_2$), preferably in the form of fumed silica, in protective adhesive pastes for use with ostomy appliances, which are composed of mixtures of hydrocolloid gums and solutions of film-forming resins. More specifically, the resistance of such pastes to the action of intestinal fluids and/or urine is markedly increased by incorporating from 2 to 6% by weight of fumed silica or other high surface area silica material. The desired liquid-tight sealing engagement of the ostomy device is more effectively maintained and for longer periods of time. In addition, the stability of the paste preparations and their shelf-life prior to application are significantly improved.

Protective adhesive paste formulated in accordance with present invention can be advantageously used in a variety of ostomy applications. The paste can be used in conjunction with every type and form of molded ostomy barriers (rings, blankets, etc.). Further, the paste can be applied in various ways, such as on, under, or next to the other barrier material. In addition, for certain applications, the paste may be used as the only barrier material, being formed into a skin blanket, ring, or other form of barrier by itself. Also, the paste will have an application for use around other surgical fluid drainage openings besides stomas, such as a wound or surgical incision.

DETAILED DESCRIPTION

The present invention is believed to be generally applicable to the protective adhesive pastes for use with ostomy appliances of the kind which are formulated as mixtures of one or more water-absorbing particulate hydrocolloid gums with an organic solvent solution of one or more adhesive film-forming resins. For example, the hydrocolloid gum may be the commonly used karaya gum, but other hydrocolloid gums can be used advantageously as a partial or complete substitute for karaya. The class of water-absorbing hydrocolloid gums is well known and such gums have comparable properties. For example, useable hydrocolloid gums include: plant exudate gums like zedou, ghatti, arabic, and tragacanth; plant extract gums like pectin; plant seed gums like guar and locust bean; and seaweed extract gums like carrageenan. Other gums, such as cellulose and cellulose derivative gums may also be used, such as carboxymethyl cellulose and hydroxyethyl cellulose. Such hydrocolloid gums are characterized by being polysaccharides, and by being hydrophilic and water-absorbing. Where it is desired to replace part of the hydrocolloid gums with a filler-type ingredient, kaolin can be added.

For the purpose of the present invention, the hydrocolloid gums are used in a fine particulate form, that is, as powders. For example, the gums may be employed in a sufficiently fine state of subdivision so that they will pass a 100 mesh or finer screen. The powdered gums as used are air-dry, that is, dry to the touch, but may contain some moisture. For example, karaya gum powder may contain from 10 to 18% by weight moisture.

The adhesive film-forming resins should be non-toxic and applicable to the skin. Suitable resins are those which can be used as medical adhesives. The resins should be soluble in alcohol or other volatile organic solvent which can be used in the formulation. The resins must be film-forming, that is, on evaporation of the solvent, a resin film, will be formed. For example, particularly desirable resins include the monoester resins sold by GAF Corporation, Chemical Division, New York, N.Y. as the "Gantrez ES" resins. In terms of chemical structure, these resins are alkyl monoesters of poly (methyl vinyl ether/maleic acids). The alkyl groups may be ethyl, isopropyl, or butyl. These resins are soluble in the lower primary alcohols, and are supplied in alcohol solution, so they are readily adapted for use in preparations of the present invention. A desirable Gantrez resin for use with karaya is sold under the code designation "ES-335-I". It is the isopropyl monoester and is supplied as 50% solution in isopropanol. Other of the Gantrez resins, such as "ES-225" are supplied as solutions in ethanol. (ES-225 is the ethyl monoester.) For the purpose of the present invention, both isopropanol and ethanol are especially desirable solvents. Other film-forming resins may be used instead of or in addition to the above-described monoester resins. For example, polyvinyl pyrrolidone has similar properties. One suitable commercial product is the "K-30" polyvinyl pyrrolidone product of GAF, which has a molecular weight of about 40,000. (GAF Corp., Chemical Division, New York, N.Y.). Polyvinyl acetate resin can also be used, such as "Resyn 28-1310" of National Starch and Chemical Corp., Chicago, Ill. To increase the flexibility of the dried resin film, the resin or mixture of resins may be plasticized by incorporating a suitable plasticizer such as propylene glycol, and/or glycerin.

The organic solvent for dissolving the resin is preferably ethanol, isopropanol, or mixtures thereof. However, other volatile organic solvents in which the resins are soluble can be employed, providing the solvent is non-toxic and applicable to the skin. There the resin is supplied as an ethanol or isopropanol solution it is convenient to use an additional amount of the same alcohol to complete the solvent system. To reduce the stinging sensation caused by applying ethanol or isopropanol to the skin, a small amount of benzyl alcohol may be added or other ingredient tending to produce a temporary anesthetic effect on the skin. See *J. Soc. Cosmet. Chem.*, 30, 415-427 (1979).

In general, the ingredients are combined in the required proportions to produce a paste, which is relatively stiff and yet readily spreadable. For example in one embodiment, from 40 to 70 parts by weight of the resin can be used per 100 parts of the karaya. In other embodiments, more of the resins (especially when a resin plasticizer is used) may be present than hydrocolloids, such as from 30 to 60 parts by weight of the hydrocolloid gums per 100 parts of the resins. Sufficient alcohol or other volatile organic solvent will be used to form a paste of the desired consistency. As indicated, the resin will be dissolved in the solvent, and the hydrocolloid particles dispersed in the resin solution. For example, from 150 to 175 parts by weight of isopropanol may be used per 100 parts of resin.

In accordance with the present invention a colloidal silica material is incorporated in the paste preparations to provide increased resistance to urine and/or intestinal fluids. Fumed silica is preferred, although precipitated silica can also be used. Fumed silica is produced by flame hydrolysis of silicon tetrachloride. It can be obtained from various manufacturers, including the Cab-O-Sil products of Cabot Corporation, Boston, Mass., and the Aerosil products of Degussa, Inc., New York, N.Y. These products are colloidal silicon dioxide of very high surface areas. They are supplied as dry white powders. For example, one suitable specific product is the Grade M-5 of Cab-O-Sil. Colloidal silica formed by precipitation from aqueous solutions are also available commercially. These products have the general formula $SiO_2 \cdot xH_2O$. One suitable product is Quso G-30 of Philadelphia Quartz, Valley Forge, Pa.

In general, from 2 to 6% by weight of the fumed silica or other colloidal silica should be incorporated in the paste product. Since the silica has a thickening action on the preparation, the maximum useable amount is limited if the desired paste-like consistency of the product is to be maintained. Fortunately, for the purpose of the present invention, the desired improvement in endurance properties appears to be optimized in the range of about 3 to 5% by weight, and in this range the paste character of the preparation can be maintained. It will be understood, however, that where necessary the amount of solvent can be increased, or the resin or hydrocolloid solids decreased to maintain the paste form of the product.

In combining the ingredients to produce the paste, the order of addition is not highly critical. However, it is advantageous to first form the solvent solution of one or more of the resin ingredients, then add the silica, and finally the hydrocolloid. Where other minor ingredients are to be incorporated, these can first be dissolved in a portion of the alcohol, and the silica can be dispersed therein before combining with the alcohol solution of the resins. Whatever the order of addition of the other ingredients, it is desirable to add the hydrocolloids last.

Other minor ingredients which may be included are solvents or co-solvents such as glycerine or propylene glycol, and preservatives or anti-bacterial agents, such as methyl or butyl paraben (para-hydroxy benzoate). Propylene glycol may also function as a plasticizer for the resins. A small amount of water may also be added,, but this is not usually necessary and provides no advantage unless ingredients are to be incorporated which are water-soluble but not alcohol-soluble. Ingredients for promoting skin healing and reducing skin irritation can also be added. Allantoin is particularly desirable for this purpose. In general, the combined minor ingredients will constitute less than 10% by weight of the complete formulation. For example, the resin, the alcohol solvent, and the hydrocolloid may comprise 80% or more of the formulation, with the amount of colloidal silica being less than 6%.

The practice of the present invention in several presently preferred embodiments are illustrated by the following examples.

EXAMPLE I

A karaya adhesive paste for use with ostomy appliances is prepared according to the following Formula A.

| Formula A | |
|---|---|
| Ingredient No. | Wt. % |
| (1) Isopropanol | 12.8 |
| (2) Glycerine (USP 99%) | 7.0 |
| (3) Methylparaben | 0.14 |
| (4) Butylparaben | 0.06 |
| (5) Fumed silica | 4.0 |
| (6) Isopropanol solution of film-forming resin (50%) | 40.0 |
| (7) Gum karaya powder | 36.0 |
| | 100.00 |

In compounding the above ingredients, ingredients 1 to 4 may be first mixed, the methyl and butylparaben dissolving in the part of the isopropanol employed for this purpose. Ingredient 5, the fumed silica, is then mixed into the solution of ingredients 1 to 4, and thoroughly dispersed therein. Next, ingredient 6, the isopropanol solution of the resin is added. Since the resin is a 50% solids solution in isopropanol, the total of isopropanol in the formula is approximately 32.8% (12.8%+20.0%). As a final step, ingredient 7, the gum karaya powder, is mixed into the solution of ingredients 1 to 6. The mixing is continued until a smooth, homogenous paste is obtained.

In the foregoing example, the fumed silica is Cab-O-Sil M-5 (Cabot Corporation, Boston, Mass.). The resin solution is Gantrez ES-335-I (GAF Corporation, Chemical Division, New York, N.Y.). The gum karaya is in the form of a powder passing a 140 mesh screen, and may contain from 10 to 18% moisture.

EXAMPLE II

The karaya paste of Example I was compared for endurance properties with a commercial karaya paste product manufactured by Hollister Incorporated, Chicago, Ill. The commercial product was composed primarily of gum karaya in admixture with an isopropanol solution of the same film-forming resin identified in Example I (Gantrez ES-335-I). Both preparations were compared as freshly prepared, and after seven weeks of room temperature storage. For the test, the simulated intestinal fluid was prepared as described in U.S.P. XIX "Intestinal Fluid, Simulated, TS," pg. 765 (1974). The simulated urine was prepared as described in *Remington's Pharmaceutical Sciences*, "Urine", pg. 598-9, Ed 15 (1975).

In preparing the samples, ribbons of the paste were extruded from tubes having 5/16 inch orifices onto silicon release paper. The test pasted ribbons had lengths of approximately 1 inch, they were standardized to a uniform weight of 3 grams. After air-drying at room temperature for 20 to 24 hours, the paste ribbons had solidified to a rigid condition, which permitted them to be handled and placed in the test apparatus.

The test apparatus includes a tank for containing the simulated intestinal fluid or urine, and a plurality of tripod testing fixtures, which may be placed in the tank in contact with the solution. The testing fixture has a platform at the top with a sample-receiving recess. The center portion of the recess is cut-out to provide an opening through the platform. When placed in test position, the solidified paste ribbons bridge the openings. U-shaped weights are then placed over the ribbons, these weights in the form of steel hooks weighing approximately 7.4 grams. In use, the hooks are placed over the samples so that when the hooks break through the samples they would fall freely through the openings in the platforms. Nylon strings are attached to the upper cross-arm portions of the inverted U-shaped hooks and the strings are attached to the operating levers of micro switches, the lengths of strings being selected so that when the sample is broken, the micro switch will be activated, and a timing clock for the particular sample will be stopped. In starting the test, after the samples have been placed in the tank and the strings attached to the micro switch levers, the simulated urine or intestinal fluid is added to the tanks to a level above the position of the samples, and the timing clocks for each sample are started. The elapsed time for breakthrough of each sample is thereby automatically recorded. The results of the test are summarized below in Table A.

TABLE A

| | Time (Hours to Break-Thru) | | | |
|---|---|---|---|---|
| | Commercial | | Example I | |
| Test Solution | Fresh | 7 wks | Fresh | 7 wks |
| Urine | 0.26 | 1.95 | 168+ | 168+ |
| Intestinal Fluid | 0.20 | 0.50 | 168+ | 168+ |

In Table A the designation "168+" indicates that the test with the Example I preparation, both as freshly prepared and after seven weeks of aging, were discontinued after an elapsed time of 168 hours. Since no breakthroughs had occurred by that time, further testing was discontinued. Each of the reported values in Table A represent three samples, the average times being shown.

The results with respect to the commercial preparation indicate that the preparation was somewhat more resistant to the simulated urine and the simulated intestinal fluid after it had aged for seven weeks. However, the aging involves some separation of the preparation so that it was no longer homogeneous. Such separation is undesirable. By way of comparison, the Example I preparation was stable and homogeneous after as long as one year of storage.

EXAMPLE III

As an alternate to the presently preferred karaya formulation of Example I, another embodiment of a karaya paste can be prepared according to the following Formula B.

| Formula B | |
|---|---|
| Ingredient No. | Wt. % |
| (1) Isopropanol | 22.8 |
| (2) Glycerine (USP 99%) | 17.0 |
| (3) Methylparaben | 0.14 |
| (4) Butylparaben | 0.06 |
| (5) Fumed silica | 4.0 |
| (6) Polyvinyl pyrrolidone (PVP) | 20.0 |
| (7) Gum karaya powder | 36.0 |
| | 100.00 |

The PVP ingredient in the above formula may be the "K-30" product of GAF Corp., described previously. The ingredients for the above formula may be compounded in the same manner as described with respect to the corresponding ingredients of Example I.

With reference to the formulas of Examples I and III, it should be understood that other hydrocolloid gums in powder form may be substituted for the gum karaya. The substitution may be on an equal weight basis, or more or less of the substitute gum may be used. On this basis, useable hydrocolloid gums include ghatti, arabic, tragacanth, pectin, guar, locust bean, carrageenan, zedou, sodium carboxymethyl cellulose, and similar gums. In other variations, ethanol may be substituted on an equal weight basis for the isopropanol, and Gantrez ES-225 may be used therewith.

EXAMPLE IV

A presently preferred non-karaya formulation using a mixture of resins and plasticizer is prepared according to the following Formula C.

| Formula C | |
|---|---|
| Ingredient No. | Wt. % |
| (1) Glycerin | 6.00 |
| (2) Propylene glycol | 20.15 |
| (3) Butylparaben | 0.2 |
| (4) Methyparaben | 0.2 |
| (5) Benzyl alcohol | 4.0 |
| (6) Gantrez ES-425 (50% ethanol) | 35.0 |
| (7) Cab-O-Sil M-5 | 4.0 |
| (8) Allantoin | 0.2 |
| (9) Kaolin | 4.0 |
| (10) Pectin | 5.0 |
| (11) Gelatin | 0.25 |
| (12) Polyacrylamide | 10.0 |
| (13) Carboxymethyl cellulose (CMC) | 9.0 |
| (14) Polyvinyl pyrrolidone (PVP) | 2.0 |
| | 100.00 |

In the foregoing formula, the hydrocolloids are pectin, gelatin, and CMC. Kaolin is a filler used in place of additional hydrocolloid. The resins are the Gantrez ES-425 (identified above), the polyacrylamide and the PVP. The organic solvent is the ethanol (provided with the Gantrez). Benzyl alcohol acts as a co-solvent and provides a temporary anesthetic effect. The propylene glycol and the glycerin are plasticizers. Cab-O-Sil M-5 is the fumed silica product previously identified. The PVP is the "K-30" product of GAF (previously identified), and the polyacrylamide is the "Reten 210 PX" product of Hercules, Inc., Wilmington, Del.

In Formulas B and C, polyvinyl acetate can be substituted for the polyvinyl pyrrolidone. For compounding the ingredients of Formula C, it is convenient to prepare a Gantrez by first blending and mixing ingredients 1–5 and then mixing with the Gantrez (ingredient 6) to produce a batch mix, which will comprise 65.55% by weight of the formula. The batch mix in this proportion is then mixed and blended with ingredients 7 and 8, and then with the remaining ingredients 9 to 14, the mixing being continued until a smooth homogeneous paste is obtained.

The products of the foregoing examples may be sterilized by gamma irradiation, for example, by using Cobalt-60 as the irradiation source. Depending on the intensity of the irradiation, some of the hydrocolloid may be degraded. However, such sterilization can be carried out without any serious impairment of the properties of the products. Further, when the product contains a polyacrylamide resin, as in Formula C of Example IV, the irradiation will cause cross-linking of the resin, which may improve the properties of the pastes, especially their resistance to the action of urine or intestinal fluid. See U.S. Pat. Nos. 4,115,339 and 4,258,715.

I claim:

1. A protective adhesive paste applicable to skin in paste form for use with ostomy appliances which provides increased resistance to urine and intestinal fluids, said paste being composed essentially of a mixture of a water-absorbing particulate hydrocolloid gum and a volatile organic solvent solution of an organic solvent-soluble adhesive film-forming resin, wherein the improvement comprises having present in said paste form 2 to 6% by weight of colloidal silica selected from the class consisting of fumed silica and precipitated silica.

2. The paste of claim 1 in which said silica is fumed silica.

3. The paste of claim 1 or claim 2 in which said paste contains from 3 to 5% by weight of said silica.

4. A karaya adhesive paste applicable to skin in paste form for use with ostomy appliances which provides increased resistance to urine and intestinal fluids, said paste being composed essentially of a mixture of karaya powder and a volatile alcohol solution of an alcohol-soluble adhesive film-forming resin, wherein the improvement comprises having present in said paste from 2 to 6% by weight of fumed silica.

5. The paste of claim 4 in which said paste contains from 3 to 5% by weight of said silica.

6. The paste of claim 4 or claim 5 in which said resin is an alkyl monoester of poly(methyl vinyl ether/maleic acid).

7. A protective adhesive paste applicable to skin in paste form for use with ostomy appliances which provides increased resistance to urine and intestinal fluids, said paste being composed essentially of a mixture of karaya powder and a volatile alcohol solution of an alkyl monoester of poly (methyl vinyl ether/maleic acid), from 40 to 70 parts by weight of said resin being present per 100 parts of said karaya powder, wherein the improvement comprises having present in said paste from 2 to 6% by weight of fumed silica.

8. The protective paste of claim 7 in which said paste contains from 3 to 5% by weight of said fumed silica.

9. A protective adhesive paste, comprising in a homogeneous admixture a volatile organic solvent component, a film-forming resin component dissolved in said solvent component, and a hydrocolloid gum component in particulate form dispersed in said paste, said components being respectively one or a plurality of different solvents, resins, and hydrocolloid gums, said paste being further characterized by containing from 2 to 6% by weight of fumed silica.

10. The paste of claim 9 further characterized by containing a plasticizer for said resin component.

11. The paste of claim 10 further characterized by said plasticized resin component comprising a mixture of an alkyl monoester of poly(methyl vinyl ether/maleic acid), polyacrylamide, and a resin selected from the class consisting of polyvinyl pyrrolidone and polyvinyl acetate.

12. A protective adhesive paste, comprising in a homogeneous admixture a volatile alcohol solvent component composed of one or a plurality of different alcohols, a film-forming resin component dissolved in said solvent component and comprising a mixture of an alkyl monoester of poly(methyl vinyl ether/maleic acid), polyacrylamide, and a resin selected from the class consisting of polyvinyl pyrrolidone and polyvinyl acetate, a plasticizer for said resin component, and a hydrocolloid gum component in particulate form dispersed in said paste, said gum component comprising a plurality of hydrocolloid gums selected from the class consisting of pectin, gelatin, carboxymethyl cellulose, and karaya, said paste being further characterized by containing from 2 to 6% by weight of fumed silica.

13. The paste of claim 12 in which said plasticizer is propylene glycol.

14. The paste of claim 12 or claim 13 in which said paste contains from 3 to 5% by weight of said fumed silica.

* * * * *